United States Patent [19]

Katsuragi et al.

[11] Patent Number: 4,686,206

[45] Date of Patent: Aug. 11, 1987

[54] COMPOSITION FOR ACTIVATING FUNCTION OF PHAGOCYTES

[75] Inventors: Yasuhiro Katsuragi, Ibaraki; Naoki Matsuda, Kobe; Yoshiko Saiga, Minoh; Yasunobu Kobayashi; Masakazu Nakamura, both of Takatsuki; Toshio Satoh, Tokushima, all of Japan

[73] Assignee: Sunstar Kabushiki Kaisha, Takatsuki, Japan

[21] Appl. No.: 800,768

[22] Filed: Nov. 22, 1985

[30] Foreign Application Priority Data

Nov. 28, 1984 [JP] Japan .................. 59-252247

[51] Int. Cl.$^4$ ............................................ A61K 31/70
[52] U.S. Cl. ...................................... 514/27; 536/4.1; 536/8; 536/18.1
[58] Field of Search .................. 514/27; 536/4.1, 8, 536/18.1

[56] References Cited

U.S. PATENT DOCUMENTS 2,616,889  11/1952  Velluz et al. .................. 536/18.1

FOREIGN PATENT DOCUMENTS 0056994  4/1985  Japan .................. 514/27

Primary Examiner—Johnnie R. Brown
Assistant Examiner—F. T. Moezie
Attorney, Agent, or Firm—Wegner & Bretschneider

[57] ABSTRACT

A pharmaceutical or veterinary composition for activating the function of phygocytes comprising as an effective ingredient a certain tocopheryl glycoside. The composition is useful for treating infectious diseases and malignant tumor.

4 Claims, No Drawings

COMPOSITION FOR ACTIVATING FUNCTION OF PHAGOCYTES

FIELD OF THE INVENTION

The present invention relates to a composition for activating the function of phagocytes. More particularly, it relates to a pharmaceutical or veterinary composition which contains as an active ingredient a certain tocopheryl glycoside and is useful for treating bacterial or viral infections in human and other mammals by activating the function of phagocytes. A method for activating the function of phagocytes is also included in the present invention.

BACKGROUND OF THE INVENTION

Phagocytes such as neutrophils, etc. play an important role in biophylaxis by phagocytosis, digestion and detoxication of foreign substances from the outside. Recently, it has been found that, in a host suffering from bacterial or viral infections, lowering of the function of phagocytes, lymphocytes and the like is observed and, when the function of them is lowered, such a host is liable to get infections and infections are liable to become severe. From this point of view, various studies relating to activation of the function of phagocytes and lymphocytes have been made and some drugs useful for activating the function of lymphocytes have been already developed and used in the treatment of and infectious diseases. However, for activating the function of phagocytes, only a few compounds, such as levamisole, have been known.

On the other hand, during the study of pharmacological activities of tocopheryl glycosides, the present inventors have surprisingly found that certain tocopheryl glycosides are useful for augmenting migration and phagocytosis of phagocytes such as neutrophils and thereby the function of phagocytes are activated.

OBJECTS AND SUMMARY OF THE INVENTION

One object of the present invention is to provide a composition for activating the function of phagocytes.

Another object of the present invention is to provide a method for activating the function of phagocytes.

These objects as well as other objects and advantages of the present invention will become apparent to those skilled in the art from the following description.

According to the present invention, there is provided a composition for activating the function of phagocytes which comprises a compound of the formula:

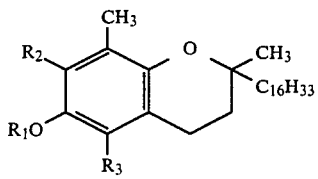

[I]

wherein $R_1$ is a glucose or mannose residue; $R_2$ and $R_3$ are, the same or different, hydrogen or methyl, and a pharmaceutically or veterinary acceptable carrier or diluent. The compound of the formula [I] is composed of tocopherol and a sugar which are commonly used in drugs and food and, therefore, toxicity of the compound is very low. The composition for activating the function of phagocytes of the present invention is useful in treatment of infectious diseases by administrating it to human or other mammals orally, parenterally or externally. Thus, the method for activating the function of phagocytes of the present invention comprises orally or parenterally administering or topically applying the compound of the formula [I], preferably, in the form of the above composition, to a human subject or other mammals requiring activation of the function of phagocytes.

DETAILED DESCRIPTION OF THE INVENTION

In the formula [I], the group $—C_{16}H_{33}$ at 2-position in the 3,4-dihydrobenzopyran ring represents 4,8,12-trimethyltridecyl group of the side chain at the 2-position of tocopherol. Further, although there exist isomers in the sugar introduced into the hydroxy group at 6-position, all the isomers including the mixture of the isomers and the isolated isomer are fallen within the scope of formula [I]. The compound of the formula [I] wherein $R_1$ is glucose residue has been already known in the prior art (The 103rd Annula Meeting of The Pharmaceutical Society of Japan, Apr. 4–6, 1983). Further, the compound of the formula [I] is disclosed in the co-pending Japanese Patent Application No. 151895/1984 assigned to the present assignee as an antiallergic agent. However, it is believed that the compound of the formula [I] has not been used heretofore in the prior art for activating the function of phagocytes.

In the present invention, preferably, both $R_2$ and $R_3$ in the formula [I] are methyl. That is, the preferred compound of the formula [I] is $\alpha$-tocopheryl glycoside. The representative examples of the compound of the formula [I] are dl-$\alpha$-tocopheryl glucoside and dl-$\alpha$-tocopheryl mannoside.

The compound of the formula [I] is prepared according to the method described in the above Japanese Patent Application No. 151895/1984.

That is, tocopherol is reacted with an appropriate peracetylated sugar in an appropriate solvent at an elevated temperature, for example 80° to 100° C., for an appropriate period of time, for example, 3 to 7 hours. By this reaction, the corresponding acetylated sugar residue is introduced at the 6-position to give an acetylated derivative which is an intermediate for the preparation of the compound of the formula [I]. The reaction proceeds preferably by using ethylene glycol diacetate or nitrobenzene as a solvent and adding p-toluenesulfonic acid as a catalyst.

Tocopherol used as the starting material may be any one of $\alpha$-, $\beta$-, $\gamma$- and $\delta$-tocopherols. The peracetylated sugar is known or is prepared by acetylating the desired sugar according to a conventional acetylation method.

The compound of the formula [I] can be prepared by deacetylating the acetylated derivative thus obtained according to a known method, for example, by heating it under reflux in absolute methanol in the presence of sodium methoxide and then treating with an ion-exchange regimen such as Amberlite IR-120 (H+ type). The compound of the formula [I] is obtained as a stable crystalline material which is soluble in an organic solvent such as alcohol, chloroform, benzene, etc. and insoluble in water and can be further purified by a conventional method such as recystallization, etc.

The compound of the formula [I] thus obtained has very low toxicity. For example, both dl-$\alpha$-tocopheryl glucoside and dl-$\alpha$-tocopheryl mannoside show $LD_{50}$ values in rat of ≧5000 mg/kg (p.o.) and ≧500 mg/kg (i.p.).

Thus, the composition for activating the function of phagocytes of the present invention can be prepared in the dosage form suitable for oral, parenteral or external administration such as tablets, powders, granules, syrups, injectable preparations, eye lotions, ointments, creams, emulsions, aqueous alcoholic solutions and the like by incorporating a non-toxic but effective amount of the compound of the formula [I] with one or more pharmaceutically or veterinary acceptable carriers or diluents such as binders, disintegrators, lubricants, solvents, agents for making isotonic, emulsifiers, suspending agents, stabilizers and the like according to a conventional pharmaceutical or veterinary technique. Preferably, the composition of the present invention is formulated in a dosage unit form containing 1 to 100 mg of the compound of the formula [I].

The composition for activating the function of phagocytes of the present invention can be administered to human subjects or other mammals orally, parenterally or externally for treating infectious diseases. For example, in case of treating human subjects, the composition is very useful for the treatment of infectious diseases caused by abnormality of the function of phagocytes such as Chediak-Higashi syndrome, lazy leukocyte syndrome, chronic granulomatosis and juvenile periodontitis.

The method for activating the function of phagocytes of the present invention is carried out by orally or parenterally administering or topically applying the compound of the formula [I], preferably, in the form of the above composition, to a human subject or other mammals requiring activation of the function of phagocytes. The dosage can be appropriately chosen according to conditions to be treated, the route of administration. However, usually, it is preferable to administer 1 to 100 mg/kg of the compound of the formula [I] per a single dose with daily dosage regimen of 100 to 1000 mg/kg of the compound of the formula [I].

The following reference examples and examples further illustrate the present invention in detail but are not to be construed to limit the scope thereof.

REFERENCE EAMPLE 1

6-O-(β-2,3,4,6-Tetraacetylmannopyranocyl)-dl-α-tocopherol dl-α-Tocopherol (10 g, 23.25 mmol) and β-D-mannopyranose pentaacetate (3.3 g, 8.46 mmol) were dissolved in nitrobenzene (5 ml) and p-toluenesulfonic acid (75 mg, 0.44 mmol) was added to the solution. The reaction system was displaced with nitrogen and was reacted in an oil bath at 90° C. under reduced pressure of 20 mmHg.

The progress of the reaction was followed by thin layer chromatography (developing solvent: benzene-ethyl acetate (10:1)). After 5 hours, benzene (100 ml) was added to the reaction mixture and the mixture was washed with water (3×100 ml) and a saturated aqueous solution of sodium chloride (3×100 ml). The benzene layer was dried with anhydrous sodium sulfate and evaporated under reduced pressure to give a dark brown oily product (13 g).

This material (13 g) was chromatographed on a column of silica gel (550 g) and eluted with benzene-ethyl acetate (9:1) to give the title product (2.4 g, 38%) as a yellow oil.

TLC [benzene-ethyl acetate (10:1)]: Rf=0.3 (single spot).
IR $\nu_{max}^{KBr}$: 1756 (C=O) cm$^{-1}$.
MS: m/Z 760 (M+).

REFERENCE EXAMPLE 2 dl-α-Tocopherylmannoside

The product (2.4 g, 3.12 mmol) of Reference Example 1 was dissolved in dry methanol (8 ml) and 0.1N sodium methoxide (2 ml) was added to the solution. The mixture was heated under reflux in a water bath. After 5 minutes, the reaction mixture was cooled and neutralized with Amberlite IR-120 (H+ type). After decolorization with charcoal, the reaction mixture was filtered and the filtrate was evaporated under reduced pressure to give the title compound (1.23 g, 68%) as white crystals.

The crystals thus obtained were further recrystallized from acetone to give the further purified title compound (0.95 g, 19%).
m.p. 128°–130° C.
TLC [chloroform-methanol (5:1)]: Rf=0.3.
IR $\nu_{max}^{KBr}$: 3390, 1160 (OH; sugar) cm$^{-1}$.
MS: m/Z 592 (M+).

REFERENCE EXAMPLE 3

6-O-(β-2,3,4,6-Tetraacetylmannopyranocyl)-d-δ-tocopherol d-δ-Tocopherol (10 g, 25 mmol) and β-D-mannopyranose pentaacetate (3.3 g, 8.86 mmol) were dissolved in nitrobenzene (5 ml) and p-toluenesulfonic acid (80 mg, 0.5 mmol) was added to the solution.

The reaction system was displaced with nitrogen and was reacted in an oil bath at 80° C. under reduced pressure of 20 mmHg. After 4 hours, benzene (100 ml) was added to the reaction mixture and the mixture was washed with water (3×100 ml) and a saturated aqueous solution of sodium chloride (3×100 ml).

The benzene layer was dried with anhydrous sodium sulfate and evaporated under reduced pressure to give a dark brown oily product (20 g).

This material (20 g) was chromatographed on a column of silica gel (550 g) and eluted with benzene-ethyl acetate to give the title product (3.8 g, 61%) as a yellow oil.

TLC [benzene-ethyl acetate (10:1)]: Rf=0.3 (single spot).
IR $\nu_{max}^{KBr}$: 1760 (C=O) cm$^{-1}$.
MS: m/Z 732 (M+).

REFERENCE EXAMPLE 4 d-δ-Tocopherylmannoside

The product (3.8 g, 5.2 mmol) of Example 3 was dissolved in dry methanol (8 ml) and 0.1N sodium methoxide (2 ml) was added to the solution.

After 5 minutes, the reaction mixture was neutralized with Amberlite IR-120 (H+ type) and decolorized with charcoal. The mixture was filtered and the filtrate was evaporated under reduced pressure to give (2.1 g, 72%) of the title product as a white crystals.

The crystals obtained were recrystallized from acetone to give the purified title compound (1.36 g, 30%).
m.p. 187°–189° C.
TLC [chloroform-methanol (5:1)] Rf=0.3 (single spot).
IR $\nu_{max}^{KBr}$: 3390, 1160 (OH; sugar) cm$^{-1}$.

MS: m/Z 564 (M+).

REFERENCE EXAMPLE 5

According to the same procedure as described in the above Reference Examples, the following compounds of formula [I] were prepared by using the corresponding tocopherol and the peracethyl sugar through the corresponding acetylated derivative.

dl-α-tocopherylglucoside (m.p. 140°–141° C.).
d-δ-tocopherylglucoside (m.p. 46°–49° C.).

EXAMPLE 1

| Ingredients | Parts by weight |
| --- | --- |
| dl-α-Tocopherylglucoside | 30 |
| Calcium phosphate | 490 |
| Crystalline cellulose | 350 |
| Carboxymethyl cellulose | 120 |
| Magnesium stearate | 10 |

These ingredients were thoroughly mixed and directly tabletted to give tablets for oral administration.

| Ingredients | Parts by weight |
| --- | --- |
| dl-α-Tocopherylglucoside | 380 |
| Lactose | 480 |
| Polyvinyl pyrrolidone | 45 |
| Hydroxypropylcellulose | 95 |

EXAMPLE 2

According to a standard wet granulation technique, granules for oral administration was prepared from these ingredients.

EXAMPLE 3

| Ingredients | Parts by weight |
| --- | --- |
| dl-α-Tocopherylmannoside | 5 |
| Distilled water for injection | 950 |

The ingredients were admixed to prepare a solution and the solution was sterilized by filtration to obtain an injectable preparation.

EXAMPLE 4

| Ingredients | Parts by weight |
| --- | --- |
| d-δ-Tocopherylglucoside | 20 |
| Bees wax | 100 |
| Paraffin wax | 60 |
| Lanolin | 30 |
| Isopropyl myristate | 60 |
| Squalane | 80 |
| Liquid paraffin | 250 |
| Polyoxyethylenesorbitan monostearate | 18 |
| Propylene glycol | 50 |
| Borax | 7 |
| Water | 325 |

According to a standard method, an ointment was prepared from these ingredients.

EXAMPLE 5

| Ingredients | Parts by weight |
| --- | --- |
| d-δ-Tocopherylmannoside | 50 |
| Stearic acid | 20 |
| Cetanol | 5 |
| Lanolin | 20 |
| Isopropyl myristate | 20 |
| Squalane | 30 |
| Liquid paraffin | 80 |
| Polyoxyethylenecetyl ether | 17 |
| Triethanolamine | 10 |
| Glycerin | 40 |
| Flavor and Preservative | q.p. |
| Water | up to 1000 parts |

According to a standard method, an emulsion preparation was prepared from these ingredients.

The effect of tocopheryl glycosides on activation of the function of phagocytes was tested. The results are described hereinafter.

(1) The effect on migration of neutrophils

Neutrophils were separated from human peripheral blood and the effect of various tocopherylglycosides on random migration and chemotaxis of the neutrophils were measured by using Boyden chambers.

Tocopherol or a tocopheryl glycoside dissolved in 1% dimethylsulfoxide was added to a suspension containing $2.5 \times 10^6$ cells/ml of neutrophils so that a concentration of tocopherol or the tocopheryl glycoside was 1 μg/ml. After 15 minutes incubation at 37° C., the mixture was added to the upper part of the chamber. To the lower part of the chamber was added PBS in case of measuring random migration, or added $2 \times 10^{-8}$M of N-formyl-methionyl-leucyl-phenylalanine in case of measuring chemotaxis. Then, the chamber was incubated at 37° C. for 1 to 3 hours. After incubation, the filter was fixed and stained with hematoxylin, and then the number of neutrophils migrated to the bottom of the filter was counted by using a microscope. As a control, the same procedure was repeated except that tocopherol or the tocopheryl glycoside was not added. The results are shown in Table 1. In Table 1, the relative percentage of the counting obtained by addition of tocopherol or the tocopheryl glycoside is shown by taking the counting of the control as 100%.

TABLE 1

| Sample | random motoricity (%) | chemotaxis (%) |
| --- | --- | --- |
| Control | 100 | 100 |
| dl-α-Tocopherol | 82 ± 12 | 94 ± 5 |
| dl-α-Tocopherylglucoside | 98 ± 34 | 140 ± 6 |
| dl-α-Tocopherylgalactoside | 64 ± 8 | 85 ± 3 |
| dl-α-Tocopherylmannoside | 71 ± 16 | 168 ± 3 |

As is seen from Table 1, chemotaxis of neutrophils is specifically improved only by the tocopheryl glucoside having glucose or mannose residue at the 6-position of 3,4-dihydrobenzopyran ring of tocopherol, while random migration thereof is scarecely effected.

(2) The effect on phagocytosis of neutrophils

Neutrophils were separated from human peripheral blood and a suspension containing $2.5 \times 10^6$ cells/ml of neutrophils was prepared. Tocopherol or a different tocopheryl glycoside was added to 900 μl of this suspension so that the concentration of tocopherol or the tocopheryl glycoside was 1 μg/ml and the mixture was incubated at 37° C. for 15 minutes.

The suspension (100 μl) containing $1 \times 10^9$ cells/ml of opsonized *Staphylococcus aureus* (IFO 13276) labeled with fluorescein isothiocyanate was added to the mixture. The resulting mixture was incubated at 37° C. for 15 minutes. Then, the number of cells incorporated into 100 cells of neutrophils was counted by using a fluorescence microscope. As a control, the same procedure was repeated except that tocopherol or the tocopheryl glycoside was not added. The results are shown in Table 2. In Table 2, the relative percentage of the counting obtained by addition of tocopherol or the tocopheryl glycoside is shown by taking the counting of the control as 100%.

TABLE 2

| sample | phagocytosis (%) |
| --- | --- |
| Control | 100 |
| dl-α-Tocopherol | 164 ± 16 |
| dl-α-Tocopherylglucoside | 168 ± 31 |
| dl-α-Tocopherylgalactoside | 112 ± 9 |
| dl-α-Tocopherylmannoside | 219 ± 21 |

As is seen from Table 2, the tocopheryl glycoside of the formula [I] also remarkably activates phagocytosis of neutrophils.

(3) In vivo test to *Pseudomonas aeruginosa*

An aqueous injectable solution of dl-α-tocopheryl glucoside or dl-α-tocopheryl mannoside (see Example 3) was intravenously injected to ICR mice (body weight: 20 to 25 g, 10 mice per a group (5 female mice and 5 male mice)) once a day (dose: 1 mg/kg) for three days continuously. After the final injection, $2.5 \times 10^7$ cells of *Pseudomonas aeruginosa* (P-1 strain, Ikaken) were injected i.p. and the percentage of survival animuls was determined after 24 hours. As a control, the same procedure was repeated except that an equal amount of distilled water was used instead of the tocopheryl glycoside and the percentage of survival animals was determined. As the result, the percentage of survival of the control group was 0%, whereas that of the group injected with dl-α-tocopherylglucoside or dl-α-tocopherylmannoside was 20%, respectively.

From these results, it is clear that the tocoperyl glyucoside of formula [I] has an excellent activity for activating the function of phagocytes.

What is claimed is:

1. Method of activating phagocytes function in an animal subject suffering from an infectious disease, in which the said subject requires such activation, which comprises administering an effective but non-toxic amount of a compound of the formula

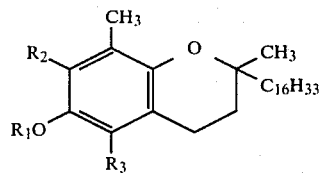

wherein $R_1$ is a glucose or mannose group and $R_2$ and $R_3$ are independently hydrogen or methyl.

2. A method of claim 1 wherein $R_1$ is a glucose group.

3. A method of claim 1 wherein $R_1$ is a mannose group.

4. A method of claim 1 wherein both $R_2$ and $R_3$ are methyl.

* * * * *